(12) United States Patent
Hupperts et al.

(10) Patent No.: US 6,559,317 B2
(45) Date of Patent: May 6, 2003

(54) METHOD FOR PRODUCTION OF A TRIAZOLINETHIONE DERIVATIVE

(75) Inventors: Achim Hupperts, Düsseldorf (DE); Michael Ruther, Langenfeld (DE); Manfred Jautelat, Burscheid (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/149,933

(22) PCT Filed: Dec. 8, 2000

(86) PCT No.: PCT/EP00/12494

§ 371 (c)(1),
(2), (4) Date: Jun. 14, 2002

(87) PCT Pub. No.: WO01/46158

PCT Pub. Date: Jun. 28, 2001

(65) Prior Publication Data

US 2003/0013890 A1 Jan. 16, 2003

(30) Foreign Application Priority Data

Dec. 21, 1999 (DE) .......................... 199 61 603

(51) Int. Cl.$^7$ ............................................. C07D 249/12
(52) U.S. Cl. ................................................. 548/263.2
(58) Field of Search ....................................... 548/263.2

(56) References Cited

FOREIGN PATENT DOCUMENTS

| DE | 40 30 039 | 3/1992 |
|---|---|---|
| EP | 0 297 345 | 1/1989 |
| WO | 99/18086 | 4/1999 |
| WO | 99/18087 | 4/1999 |
| WO | 99/18088 | 4/1999 |

OTHER PUBLICATIONS

I. Arai: "Bulletin of the Chemical Society of Japan, JP, Japan Publications Trading Co. Tokyo" Bulletin of the Chemical Society of Japan JP, Japan, JP, Japan Publications Trading Co. Tokyo Bd. 46, Nr. 7, 1, Jul. 1, 1973, Seiten 2215–2218, XP002087557 ISSN: 0009–2673 Seite 2116.
Database Chemabs 'Online! Chemical Abstracts Service, Columbus, Ohio, US; Mozolis, V. et al: "Synthesis of disulfides and sulfides containing sulfo groups" retrieved from STN Database accession No. 87:101885 XP002167238 Zusammenfassung & Liet. Tsr Mokslu Akad. Darb., Ser. B (1977), (2), 23–7.

Primary Examiner—Patricia L. Morris
(74) Attorney, Agent, or Firm—Richard E. L. Henderson; Raymond J. Harmuth

(57) ABSTRACT

According to a novel process, the triazolinethione derivative of the formula

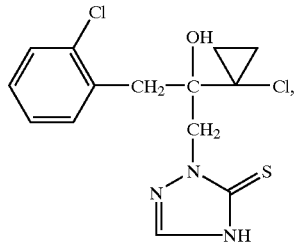

(I)

can be prepared by
a) reacting the oxirane of the formula

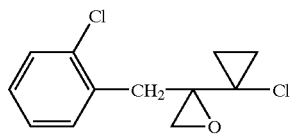

(II)

with hydrazine hydrate in the presence of specific diluents, followed by introduction of hydrogen chloride or extraction with aqueous hydrochloric acid,
b) treating the resulting hydrazine hydrochloride derivative of the formula

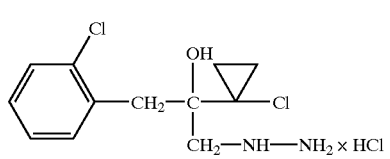

(III)

with alkali metal hydroxide in the presence of water and further specific diluents, followed by successive reaction with formaldehyde and thiocyanate of the formula

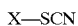

X—SCN (IV)

in the presence of certain solvents and finally
c) reacting the triazolidine derivative of the formula

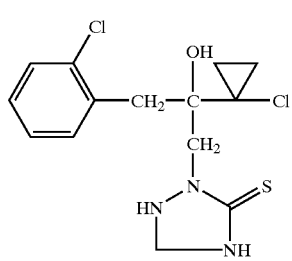

(V)

with iron(III) chloride in the presence of aqueous hydrochloric acid.

10 Claims, No Drawings

METHOD FOR PRODUCTION OF A TRIAZOLINETHIONE DERIVATIVE

This application is a 371 of PCT/EP00/12494 filed Dec. 8, 2000.

The present invention relates to a novel process for preparing 2-(1-chloro-cycloprop-1-yl)-1-(2-chloro-phenyl)-3-(4,5-dihydro-1,2,4-triazole-5-thiono-1-yl)-propan-2-ol, which is known as an active compound with microbicidal, in particular fungicidal, properties.

It is already known that 2-(1-chloro-cycloprop-1-yl)-1-(2-chloro-phenyl)-3-(4,5-dihydro-1,2,4-triazole-5-thiono-1-yl)-propan-2-ol can be prepared by initially reacting 3-chloro-2-(1-chloro-cycloprop-1-yl)-1-(2-chloro-phenyl)-propan-2-ol with hydrazine hydrate, if appropriate in the presence of an inert organic solvent, such as alcohol, ether or nitrile, then reacting the resulting 2-(1-chloro-cycloprop-1-yl)-3-(2-chloro-phenyl)-2-hydroxy-propyl-1-hydrazine with formaldehyde and alkali metal thiocyanate or ammonium thiocyanate and finally reacting the resulting 2-(1-chloro-cycloprop-1-yl)-1-(2-chloro-phenyl)-2-hydroxy-3-(1,2,4-triazolidine-5-thiono-1-yl)-propane with oxygen in the presence of sulphur and potassium hydroxide (cf. WO 99-18 087). The reaction sequence can be illustrated by the formula scheme below:

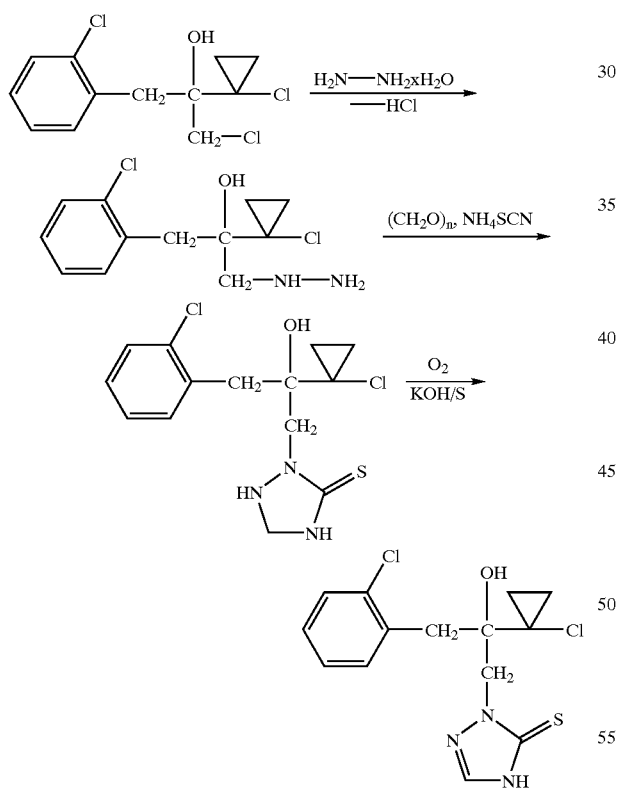

This process has the disadvantage that the hydrazine compound formed in the first step is relatively unstable in the free state. Moreover, it is unfavourable that undesirable by-products are formed in the course of the multi-step synthesis and that the yield is relatively low for a preparation on an industrial scale. Finally, it is likewise detrimental that an interfering overoxidation can take place during the third step, resulting in the elimination of sulphur from the target product.

It has now been found that 2-(1-chloro-cycloprop-1-yl)-1-(2-chloro-phenyl)-3-(4,5-dihydro-1,2,4-triazole-5-thiono-1-yl)-propan-2-ol of the formula

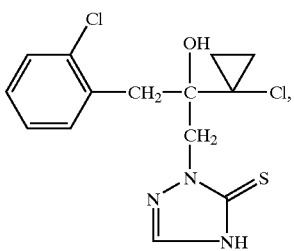

(I)

can be prepared when a) in a first step, 2-(1-chloro-cycloprop-1-yl)-2-(2'-chloro-benzyl)-oxirane of the formula

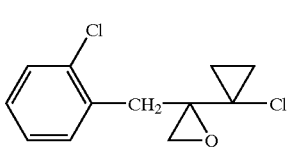

(II)

is initially reacted with hydrazine hydrate in the presence of aromatic hydrocarbon, if appropriate in a mixture with acetonitrile, and hydrogen chloride is then introduced, or the mixture is extracted with aqueous hydrochloric acid b) in a second step, the resulting 2-(1-chloro-cycloprop-1-yl)-3-(2-chloro-phenyl)-2-hydroxy-propyl-1-hydrazine hydrochloride of the formula

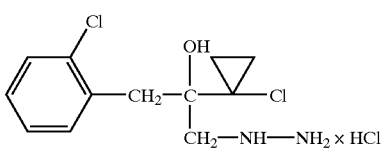

(III)

is then treated with alkali metal hydroxide in the presence of water and in the presence of aromatic hydrocarbon, if appropriate in a mixture with a lower alcohol, or in the presence of alkyl alkylcarboxylate, and then reacted successively with formaldehyde and thiocyanate of the formula $$X\text{—SCN} \qquad (IV),$$

in which x represents sodium, potassium or ammonium, in the presence of water and in the presence of aromatic hydrocarbon, if appropriate in a mixture with a lower alcohol, or in the presence of alkyl alkylcarboxylate and, if appropriate, in the presence of a catalyst, and c) in a third step, the resulting 2-(1-chloro-cycloprop-1-yl)-1-(2-chloro-phenyl)-2-hydroxy-3-(1,2,4-triazolidine-5-thiono-1-yl)-propane of the formula

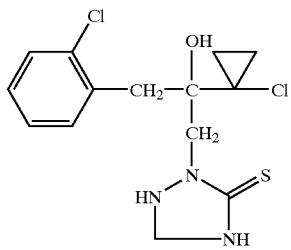

(V)

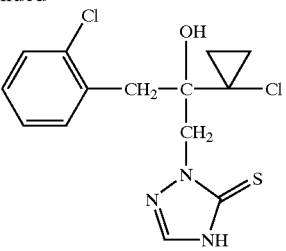

is then reacted with iron(III) chloride in the presence of aqueous hydrochloric acid and in the presence of an inert organic diluent.

It is extremely surprising that the triazolinethione derivative of the formula (I) can be prepared by the process according to the invention in higher yields than by the prior-art methods. It is also unexpected that, during the course of the multi-step synthesis, there are virtually no interfering side reactions.

The process according to the invention has a number of advantages. Thus, as already mentioned, it allows the synthesis of the triazolinethione derivative of the formula (I) in high yield. Moreover, it is favourable that the starting materials and reaction components required can be prepared in a simple manner and are available even in relatively large amounts. It is a further advantage that the individual reaction steps and the isolation of the reaction products can be carried out without any difficulties. Finally, it should also be mentioned that the hydrazine hydrochloride derivative of the formula (III), in contrast to the corresponding hydrazine compound, can be handled without any stability problems, and that an overoxidation in the last step can be avoided.

Using sodium hydroxide as neutralizing agent and sodium thiocyanate and Formalin solution as reaction components for carrying out the second step, the course of the process according to the invention can be illustrated by the following formula scheme:

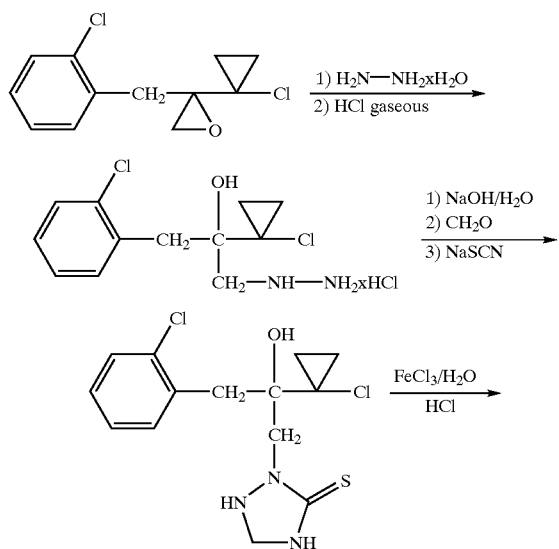

The 2-(1-chloro-cycloprop-1-yl)-2-(2'-chloro-benzyl)-oxirane of the formula (II) required as starting material for carrying out the process according to the invention is known (cf. EP-A 0 297 345). It can be prepared by reacting the chlorohydrin derivative of the formula

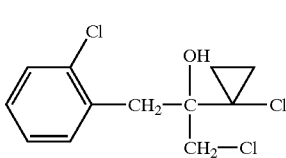

(VI)

in the presence of an acid binder, such as potassium tert-butoxide, sodium methoxide or potassium carbonate, and in the presence of a diluent, such as dimethylformamide, methanol, n-butanol, tetrahydrofuran, methyl-tert-butyl ether or toluene, at temperatures between 20° C. and 60° C.

When carrying out the first step of the process according to the invention, the oxirane of the formula (II) can be employed both in pure form and in a mixture with the chlorohydrin derivative of the formula (VI).

Aromatic hydrocarbons suitable for carrying out the first step of the process according to the invention are preferably benzene, toluene or xylene. Particular preference is given to using toluene in a mixture with acetonitrile. It is very particularly advantageous to use acetonitrile in an amount which is equimolar to that of the oxirane of the formula (II).

Both the first step and the second and third steps of the process according to the invention are generally carried out under atmospheric pressure. However, it is also possible to work under elevated pressure or, if no gaseous components take part in the reaction, even under reduced pressure.

When carrying out the first step of the process according to the invention, the reaction temperatures can be varied within a certain range. In general, the first step is carried out at temperatures between 20° C. and 150° C., preferably between 60° C. and For carrying out the first step of the process according to the invention, in general from 3 to 6 mol of hydrazine hydrate are employed per mole of oxirane of the formula (II). Specifically, oxirane of the formula (II), if appropriate in a mixture with chlorohydrin of the formula (VI), is reacted with hydrazine hydrate in the presence of toluene and, if appropriate, in the presence of an amount of acetonitrile which is equivalent to that of the oxirane of the formula (II). Work-up is then carried out by customary methods. In general, the reaction mixture is cooled to room temperature and is mixed with water, the organic phase is separated off and washed with water and an equivalent amount or else an excess of dry hydrogen chloride gas is then introduced with cooling. The resulting solid is separated off, washed with toluene, if appropriate in a mixture with a further hydrocarbon, and dried. However, it is also possible to extract the mixture with aqueous hydrochloric acid. The resulting solid is separated off, washed with toluene, if appropriate in a mixture with a further hydrocarbon, and dried.

In a preferred variant, both the first and the second step of the process according to the invention are carried out under an atmosphere of protective gas. Preferred protective gases are argon and nitrogen.

The alkali metal hydroxide used for carrying out the second step of the process according to the invention is preferably lithium hydroxide, sodium hydroxide or potassium hydroxide. Particular preference is given to using sodium hydroxide.

Preferred aromatic hydrocarbons used as diluents for carrying out the second step of the process according to the invention, both in the treatment of the hydrazine hydrochloride derivative of the formula (III) and in the subsequent reaction with formaldehyde and thiocyanate of the formula (IV), are benzene, toluene and xylene. Preferred lower alcohols are methanol, ethanol or propanol. The preferred alkyl alkylcarboxylate is ethyl acetate. Particularly preferably, both the neutralization and the subsequent reaction in the second step of the process according to the invention are carried out either in the presence of toluene in a mixture with ethanol or in the presence of ethyl acetate.

The formaldehyde required as reaction component for carrying out the second step of the process according to the invention can be employed as paraformaldehyde, as gaseous formaldehyde or else as Formalin solution (=aqueous formaldehyde solution). Preference is given to using Formalin solution.

The preferred thiocyanate for carrying out the second step of the process according to the invention is sodium thiocyanate.

Suitable catalysts for carrying out the second step of the process according to the invention are all reaction accelerators which are customary for such reactions. Preference is given to using sodium hydrogen sulphate.

When carrying out the second step of the process according to the invention, the reaction temperatures can likewise be varied within a certain range. In general, both the neutralization of the hydrazine hydrochloride derivative of the formula (III) and the further reaction are carried out at temperatures between 0° C. and 30° C., preferably between 10° C. and 25° C.

When carrying out the second step of the process according to the invention, in general an equivalent amount or else an excess of alkali metal hydroxide, from 1 to 2 mol of formaldehyde and from 1 to 2 mol of thiocyanate of the formula (IV) and, if appropriate, from 1 to 2 mol of sodium hydrogen sulphate and water are employed per mole of hydrazine hydrochloride derivative of the formula (III), where the water may also be present in excess. Work-up is carried out by customary methods. In general, the reaction mixture is admixed with water, and the organic phase is separated off, washed with saturated aqueous sodium chloride solution and with water, dried and concentrated. Any impurities that may still be present can be removed by customary methods, such as recrystallization.

Preferred inert organic diluents for carrying out the third step of the process according to the invention are ethanol, ethyl acetate or mixtures of ethanol and toluene.

When carrying out the third step of the process according to the invention, the reaction temperatures can likewise be varied within a certain range. In general, the third step is carried out at temperatures between 0° C. and 100° C., preferably between 10° C. and 65° C.

When carrying out the third step of the process according to the invention, in general an equivalent amount or else an excess of iron(III) chloride is employed per mole of triazolidine compound of the formula (V). Work-up is carried out by customary methods. In general, if appropriate after prior admixing of the reaction mixture with water, the phases are separated and the organic phase is washed, dried and concentrated. Any impurities which may still be present can be removed by customary methods, for example by recrystallization.

In a particular variant, the process according to the invention can be carried out such that steps two and three are conducted as a one-pot reaction. In this case, the mixture obtained in the second step is subjected directly, without prior isolation of the triazolidine of the formula (V), to the oxidation in the third step. However, prior to the addition of the iron(III) chloride solution, the reaction mixture obtained in the second step has to be washed thoroughly with water to remove any excess thiocyanate which may be present.

The triazolinethione derivative preparable according to the invention can be present in the "thiono" form of the formula

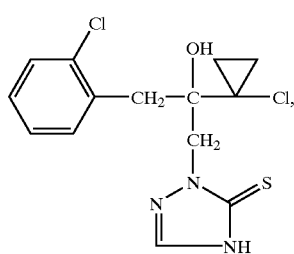

(I)

or in the tautomeric "mercapto" form of the formula

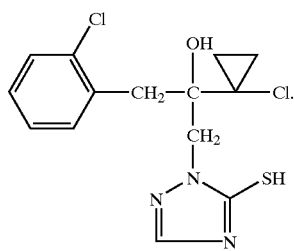

(Ia)

For the sake of simplicity, only the "thiono" form is shown in each case.

The triazolinethione derivative preparable according to the invention is known as an active compound having microbicidal, in particular fungicidal, properties (cf. WO 96-16 048).

The practice of the process according to the invention is illustrated by the examples below.

PREPARATION EXAMPLES

Example 1

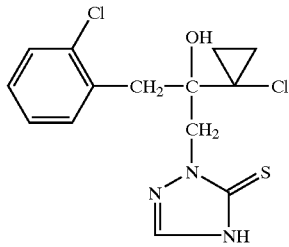
(I)

a) Preparation of the Compound of the Formula

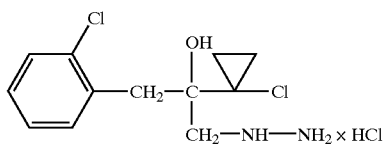
(III)

At room temperature and under an atmosphere of argon, 174 g of a solution of 0.1 mol of 2-(1-chloro-cycloprop-1-yl)-2-(2'-chloro-benzyl)-oxirane in toluene are added with stirring to a mixture of 25 ml (0.5 mol) of hydrazine hydrate and 5.2 ml (0.1 mol) of acetonitrile. With vigorous stirring, the reaction mixture is heated to 85° C. and kept at this temperature for 4 hours. The mixture is then allowed to cool to room temperature, 40 ml of water are added and the phases are separated.

The organic phase is washed twice, in each case with 20 ml of water. With cooling using dry ice, 1.5 equivalents of dry hydrogen chloride gas are then introduced. After the addition has ended, the mixture is stirred at room temperature for 16 hours. The resulting crystalline solid is separated off, washed with a little toluene and petroleum ether and dried. This gives 30.5 g of a product which, according to HPLC, comprises 97.9% of 2-(1-chloro-cycloprop-1-yl)-3-(2-chloro-phenyl)-2-hydroxy-propyl-1-hydrazine hydrochloride. Accordingly, the yield is calculated to be 95.9% of theory.

b) Preparation of the Compound of the Formula

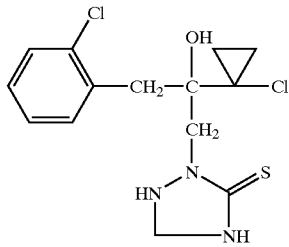
(V)

At room temperature and under an atmosphere of argon, a mixture of 93.4 g (0.3 mol) of 2-(1-chloro-cycloprop-1-yl)-3-(2-chlorophenyl)-2-hydroxy-propyl-1-hydrazine hydrochloride and 1000 ml of ethyl acetate is admixed with stirring with 12.0 g (0.3 mol) of sodium hydroxide micropills and 20 ml of water. The reaction mixture is stirred at room temperature for 1 hour and then admixed with 20.8 ml (0.276 mol of formaldehyde) of Formalin solution (36.5% strength in water). The mixture is stirred at room temperature for 30 minutes, and 23.8 g (0.294 mol) of sodium thiocyanate and 63.0 g (0.524 mol) of sodium hydrogen sulphate are then added and the mixture is stirred at room temperature for another 2 hours. 300 ml of water are then added and the phases are separated. The organic phase is washed twice with saturated aqueous sodium chloride solution and with water, and then dried over sodium sulphate and concentrated under reduced pressure. This gives 119.4 g of a solid which, according to HPLC, comprises 80.35% of 2-(1-chloro-cycloprop-1-yl)-1-(2-chloro-phenyl)-2-hydroxy-3-(1,2,4-triazolidine-5-thiono-1-yl)-propane. Accordingly, the yield is calculated to be 94.8% of theory.

c) Preparation of the Compound of the Formula

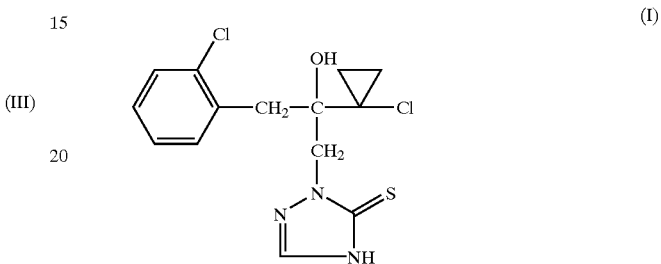
(I)

At room temperature, a mixture of 1.8 g (0.005 mol) of 2-(1-chloro-cycloprop-1-yl)-1-(2-chloro-phenyl)-2-hydroxy-3-(1,2,4-triazolidine-5-thiono-1-yl)-propane, 40 ml of toluene and 10 ml of ethanol is admixed with stirring with 20 ml (0.01 mol) of 0.5 molar aqueous iron(III) chloride solution which had been acidified slightly with hydrochloric acid. The reaction mixture is stirred at room temperature for 6 hours, and the phases are then separated. The organic phase is washed twice with water and saturated aqueous sodium chloride solution, dried over sodium sulphate and concentrated under reduced pressure. This gives 1.8 g of a solid which, according to HPLC, comprises 94.8% of 2-(1-chloro-cycloprop-1-yl)-1-(2-chloro-phenyl)-3-(4,5-dihydro-1,2,4-triazole-5-thiono-1-yl)-propan-2-ol. Accordingly, the yield is calculated to be 99.2% of theory.

Example 2

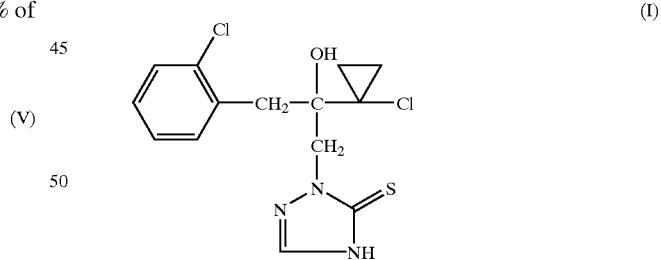
(I)

3rd Step

At room temperature, a mixture of 1.8 g (0.005 mol) of 2-(1-chloro-cycloprop-1-yl)-1-(2-chloro-phenyl)-2-hydroxy-3-(1,2,4-triazolidine-5-thiono-1-yl)-propane and 50 ml of ethanol is admixed with stirring and with cooling with 20 ml (0.01 mol) of a 0.5 molar aqueous iron(III) chloride solution which had been acidified slightly with hydrochloric acid. The reaction mixture is stirred at room temperature for another 2 hours and then poured into icewater and extracted with ethyl acetate. The organic phase is washed twice with water and saturated aqueous sodium chloride solution, dried over sodium sulphate and concentrated under reduced pressure. This gives 1.74 g of a solid which, according to HPLC, comprises 97.1% of 2-(1-chloro-cycloprop-1-yl)-1-(2-chloro-phenyl)-3-(4,5-dihydro-1,2,4-triazole-5-thiono-1-yl)-propan-2-ol. Accordingly, the yield is calculated to be 98.2% of theory.

Comparative Example A

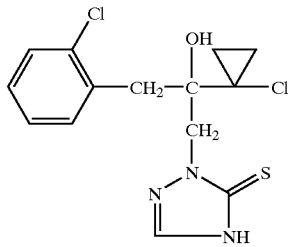

a) Preparation of the Compound of the Formula

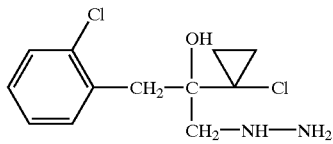

Under an atmosphere of nitrogen and with stirring, a mixture of 27.8 g (0.1 mol) of 3-chloro-2-(1-chloro-cycloprop-1-yl)-1-(2-chloro-phenyl)-propan-2-ol and 48.5 ml (1 mol) of hydrazine hydrate is heated at 100° C. for 5 hours. The two-phase system is cooled to room temperature, and the hydrazine phase is then decanted off and the residue is washed once with 20 ml of water. 25.9 g of a product which, according to gaschromatographic analysis, comprises 86.8% of 2-(1-chloro-cycloprop-1-yl)-3-(2-chloro-phenyl-phenyl)-2-hydroxy-propyl-1-hydrazine, remain. Accordingly, the yield is calculated to be 94.5% of theory. Recrystallization of the crude product from acetonitrile gives [2-(1-chloro-cycloprop-1-yl)-3-(2-chloro-phenyl)-2-hydroxy]-propyl-1-hydrazine in the form of a solid of melting point 86° C. to 88° C.

b) Preparation of the Compound of the Formula

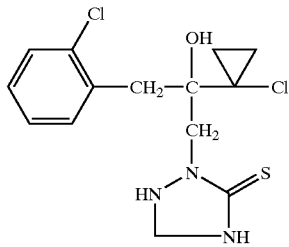

A mixture of 5.48 g (20 mmol) of [2-(1-chloro-cycloprop-1-yl)-3-(2-chloro-phenyl)-2-hydroxy]-propyl-1-hydrazine, 40 ml of methyl tert-butyl ether, 0.9 g (30 mmol) of paraformaldehyde and 1.84 g (24 mmol) of ammonium thiocyanate is heated with stirring at 60° C. for 3 hours. After cooling to room temperature, the reaction mixture is diluted with methyl tert-butyl ether and washed with saturated aqueous sodium carbonate solution. The organic phase is dried over sodium sulphate, filtered and concentrated under reduced pressure. This gives 6.1 g of a product which, according to HPLC analysis, comprises 86.9% of 2-(1-chloro-cycloprop-1-yl)-1-(2-chlorophenyl)-2-hydroxy-3-(1, 2,4-triazolidine-5-thiono-1-yl)-propane. After addition of a little dichloromethane, 2-(1-chloro-cycloprop-1-yl)-1-(2-chloro-phenyl)-2-hydroxy-3-(1,2,4-triazolidine-5-thiono-1-yl)-propane precipitates in the form of a crystalline solid.

c) Preparation of the Compound of the Formula

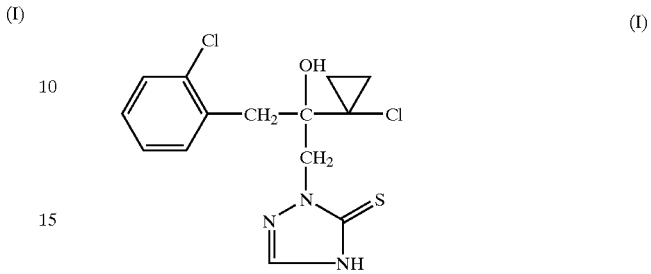

For 3.5 hours, a stream of air is passed over a stirred mixture, heated at 70° C., of 1.72 g (5 mmol) of 2-(1-chloro-cycloprop-1-yl)-1-(2-chloro-phenyl)-2-hydroxy-3-(1,2,4-triazolidine-5-thiono-1-yl)-propane, 10 ml of absolute toluene, 0.34 g (6 mmol) of potassium hydroxide powder and 10 mg of sulphur powder. The progress of the reaction is monitored by HPLC analysis. After cooling to room temperature, the reaction mixture is diluted with methyl tert-butyl ether and washed repeatedly with saturated aqueous ammonium chloride solution. The organic phase is dried over sodium sulphate, filtered and concentrated under reduced pressure. This gives 2.2 g of a product which, according to HPLC analysis, comprises 71% of 2-(1-chloro-cycloprop-1-yl)-1-(2-chloro-phenyl)-3-(4,5-dihydro-1,2,4-triazole-5-thiono-1-yl)-propan-2-ol.

What is claimed is:

1. A process for preparing 2-(1-chloro-cycloprop-1-yl)-1-(2-chloro-phenyl)-3-(4,5-dihydro-1,2,4-triazole-5-thiono-1-yl)-propan-2-ol of the Formula (I)

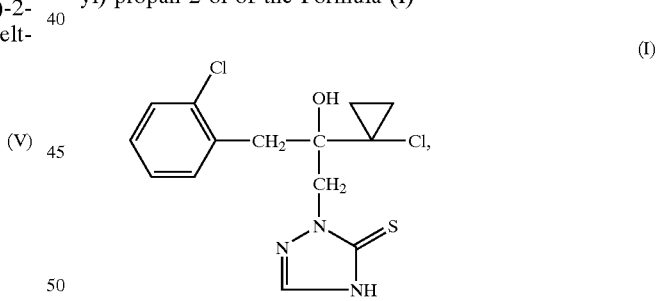

comprising the steps of:

a) in a first step, reacting 2-(1-chloro-cycloprop-1-yl)-2-(2'-chloro-benzyl)-oxirane of the Formula (II)

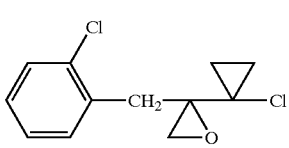

with hydrazine hydrate in the presence of aromatic hydrocarbon, optionally in the presence of acetonitrile to form a mixture, and introducing into said mixture hydrogen chloride or extracting said mixture with aqueous hydrochloric acid to form 2-(1-chloro-cycloprop-1-yl)-3-(2-chloro-phenyl)-2-hydroxy-propyl-1-hydrazine hydrochloride of the Formula (III)

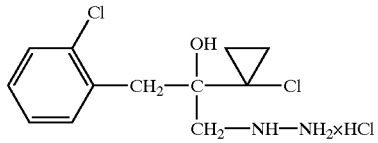

(III)

b) in a second step, treating the resulting 2-(1-chloro-cycloprop-1-yl)-3-(2-chloro-phenyl)-2-hydroxy-propyl-1-hydrazine hydrochloride of the Formula (III)

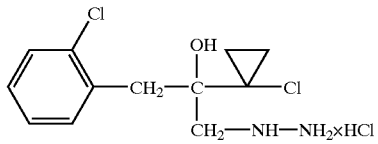

(III)

with alkali metal hydroxide in the presence of water and in the presence of aromatic hydrocarbon, optionally in a mixture with a lower alcohol, or in the presence of alkyl alkylcarboxylate, and then reacting successively with formaldehyde and thiocyanate of the Formula (IV)

X—SCN  (IV), wherein
X represents sodium, potassium or ammonium,
in the presence of water and in the presence of aromatic hydrocarbon, optionally in a mixture with a lower alcohol, or in the presence of alkyl alkylcarboxylate and, optionally, in the presence of a catalyst to form 2-(1-chloro-cycloprop-1-yl)-1-(2-chloro-phenyl)-2-hydroxy-3-(1,2,4-triazolidine-5-thiono-1-yl)-propane of the Formula (V)

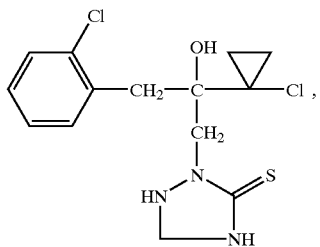

(V)

and c) in a third step, reacting the resulting 2-(1-chloro-cycloprop-1-yl)-1-(2-chloro-phenyl)-2-hydroxy-3-(1,2,4-triazolidine-5-thiono-1-yl)-propane of the Formula (V)

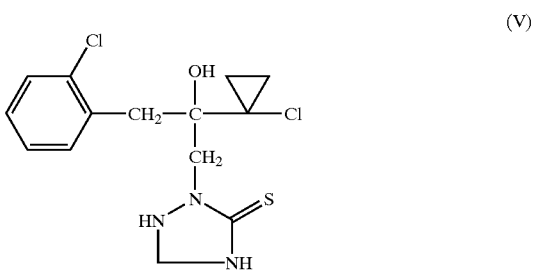

(V)

with iron(III) chloride in the presence of aqueous hydrochloric acid and in the presence of an inert organic diluent.

2. The process according to claim 1, wherein the diluent used for carrying out the first step is toluene in a mixture with acetonitrile.

3. The process according to claim 1, wherein the neutralizing agent used for carrying out the second step is sodium hydroxide.

4. The process according to claim 1, wherein the diluent used for carrying out the second step is ethyl acetate or toluene in a mixture with ethanol.

5. The process according to claim 1, wherein the formaldehyde used for carrying out the second step is employed in the form of formalin solution.

6. The process according to claim 1, wherein the reaction component and the catalyst used for carrying out the second step are sodium thiocyanate and sodium hydrogen sulphate, respectively.

7. The process according to claim 1, wherein the diluent used for carrying out the third step is ethyl acetate, ethanol or a mixture of toluene and ethanol.

8. The process according to claim 1, wherein the first step is carried out at temperatures between 20° C. and 150° C.

9. The process according to claim 1, wherein the second step is carried out at temperatures between 0° C. and 30° C.

10. The process according to claim 1, wherein the third step is carried out at temperatures between 0° C. and 100° C.

* * * * *